United States Patent [19]

Hotten

[11] 4,118,328

[45] Oct. 3, 1978

[54] AMINE PHOSPHATE SALTS

[75] Inventor: Bruce W. Hotten, Orinda, Calif.

[73] Assignee: Chevron Research Company, San Francisco, Calif.

[21] Appl. No.: 858,585

[22] Filed: Dec. 8, 1977

[51] Int. Cl.$^2$ .................. C10M 1/44; C10M 3/38; C07F 9/08; C07F 9/16
[52] U.S. Cl. .................. 252/32.5; 252/49.9; 252/400 A; 260/925; 424/199; 424/211
[58] Field of Search .................. 252/32.5, 49.9, 400 A; 260/925

[56] References Cited

U.S. PATENT DOCUMENTS

| | | | |
|---|---|---|---|
| 2,371,854 | 3/1945 | Smith et al. | 252/32.5 |
| 2,563,506 | 8/1951 | Werntz | 252/32.5 |
| 3,711,404 | 1/1973 | Redmore | 252/49.9 |
| 3,810,838 | 5/1974 | Hangen | 252/49.9 |
| 3,992,307 | 11/1976 | Hotten | 252/49.9 |

Primary Examiner—Irving Vaughn
Attorney, Agent, or Firm—D. A. Newell; C. J. Tonkin; L. L. Vaughan

[57] ABSTRACT

Phosphate salts are prepared by reacting a triaryl phosphate and an aliphatic amine in the presence of a catalytic amount of boric acid. Certain of the phosphate salts are useful as additives for lubricating oils.

9 Claims, No Drawings

AMINE PHOSPHATE SALTS

FIELD OF THE INVENTION

This invention relates to a process for preparing phosphate salts and the products prepared by this process. This invention also relates to lubricating oil compositions containing certain phosphate salts.

BACKGROUND OF THE INVENTION

Amine phosphate salts have been prepared by heating an amine and the corresponding O,O-dihydrocarbyl phosphoric acid. When trialkyl phosphates are reacted with amines, they act as alkylating agents with the product forming as illustrated below, where R and $R^1$ are alkyl:

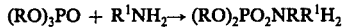

This type of reaction is illustrated in U.S. Pat. No. 2,563,506.

When R in the above reaction sequence is aromatic, no reaction between the amine and the phosphate occurs.

SUMMARY OF THE INVENTION

It has now been found that the reaction between a triaryl phosphate and a primary or secondary aliphatic amine is catalyzed by boric acid to yield rapid, selective formation of the amine phosphate salt. Certain of these amine phosphate salts are particularly useful as anti-oxidant, anti-wear and friction-modifying additives for lubricating oils.

DETAILED DESCRIPTION OF THE INVENTION

Starting Materials

Preferred triaryl phosphates for use within the scope of this invention are those of the formula

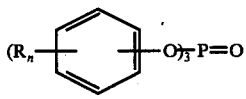

where R is alkyl, halo, alkoxy, nitro, trifluoromethyl, or dihydrocarbylamine and $n$ is 0, 1 or 2.

Preferred primary or secondary aliphatic amines are those in which the aliphatic radical contains from 4 to 18 carbon atoms.

Particularly preferred starting-material phosphates and amines for preparing the lubricating oil additives are those where R is alkyl and the aliphatic amine is a primary alkyl amine containing 12-18 carbon atoms.

As used herein, the following terms have the meaning set forth below.

"Aryl" means a compound containing at least one aromatic, 6-carbon-membered ring. It may contain other cyclo-aliphatic rings and/or any substituent groups that do not adversely affect the desired reaction path.

"Primary amine" means an amine having two hydrogen substituents and one non-hydrogen substituent that is bonded by a carbon bond to a nitrogen atom.

"Secondary amine" means an amine having one hydrogen substituent and two non-hydrogen substituents that are bonded by a carbon bond to a nitrogen atom.

"Aliphatic" means a non-aromatic, carbon-containing radical which is either saturated or unsaturated, that is, it contains one or more olefinic or acetylenic sites of unsaturation. The aliphatic radical may not contain any substituents that would adversely affect the reaction of this invention. Preferably the aliphatic group contains only carbon and hydrogen and consists of 3 to 30 carbon atoms.

"Alkyl" means a saturated aliphatic carbon chain of 1 to 30 carbon atoms which contains only carbon and hydrogen atoms.

"Halo" means fluoro, chloro, bromo or iodo.

"Alkoxy" means the radical alkyl—O— where alkyl is as defined above.

"Hydrocarbyl" means a $C_1$–$C_{30}$ aliphatic or $C_6$–$C_{30}$ aromatic hydrocarbon radical containing only carbon and hydrogen atoms.

REACTION CONDITIONS

The reaction is preferably carried out by combining in the reaction mixture from 1 to 20 mols of amine per mol of triaryl phosphate. Generally the reaction proceeds most efficiently when the molar ratio of reactants is 2-3 mols of amine per mol triaryl phosphate.

The reaction usually proceeds to completion in from 0.5 to 30 hours when a reaction temperature of 100°–200° C. is employed.

Excess amine, aromatic by-products and catalyst can be removed, if desired, from the reaction product by vacuum distillation at 100–1000 Pa (0.75–7.5 mm Hg) and a pot temperature of about 100°–170° C.

A catalytic amount of boric acid must be present in the reaction mixture. Preferably 1–5 weight percent, based on the total weight of amine and phosphate, and most preferably 3–5 weight percent boric acid is used as the catalyst.

If desired, the reaction may be carried out in the presence of a hydrocarbon diluent; however, the reaction usually proceeds satisfactorily in the absence of any solvent or diluent.

Uses

The amine phosphate salts prepared by the process of this invention have a variety of uses, such as lubricating oil additives, thickening agents, and biocides.

Lubricating Oil Compositions

The preferred salts for use in lubricating oil compositions are described above. These salts are particularly useful as anti-oxidant, anti-wear and friction-modifying additives for lubricating oils. Their use in oils reduces the power lost between sliding parts and can increase the number of miles per gallon of fuel that an engine can produce.

The lubricating oil compositions of this invention can be prepared by mixing an oil of lubricating viscosity with from 0.01 to 10% by weight of the desired phosphate salt. The amount of salt which may be present in the lubricating oil in order to impart the desired properties varies with the type of salt, the type of lubricating oil, and the presence of other additives. This type of variation is well known in the art. In general, the preferred additive concentration is 0.05–2% by weight based on the weight of the final lubricating oil composition.

The lubricating oil which may be employed in the practice of this invention includes a wide variety of hydrocarbon oils. Other oils include lubricating oils derived from coal products and synthetic oils, e.g., alkylene polymers (such as polypropylene, polybutylene, etc., and mixtures thereof), alkylene oxide-type polymers (e.g., alkylene oxide polymers prepared by polymerizing alkylene oxides such as propylene oxide, etc., in the presence of water or alcohol, e.g., ethyl alcohol), carboxylic acid esters (e.g., those which were prepared by esterifying carboxylic acids such as adipic acid, azelaic acid, suberic acid, sebacic acid, alkenylsuccinic acid, fumaric acid, maleic acid, etc., with the alcohol such as butyl alcohol, hexyl alcohol, 2-ethylhexyl alcohol, pentaerythritol, etc., liquid esters of phosphorus, such as trialkyl phosphate (tributyl phosphate), dialkylaryl phosphate, triaryl phosphate (tricresyl phosphate), etc., alkylbenzenes, polyphenols (e.g., bisphenols and terphenols, alkylbiphenylethers, esters and polymers of silicon, e.g., tetraethyl silicate, tetraisopropyl silicate, hexyl-(4-methyl-2-pentoxy) disilicate, poly(methyl)siloxane and poly(methylphenyl)siloxane, etc. The lubricating oils may be used individually or in combinations whenever miscible or whenever made so by use of mutual solvents. The lubricating oils generally have a viscosity which ranges from 50 to 5000 SUS (Saybolt Universal Seconds) and usually from 100 to 1500 SUS at 100° F. (38° C.).

In addition to the phosphate salt, other additives may be successfully employed within the lubricating compositions of this invention without affecting their high stability and performance over a wide temperature scale. One type of additive is an anti-oxidant or oxidation inhibitor. This type of additive is employed to prevent varnish and sludge formation on metal parts and to inhibit corrosion of alloyed bearings. Typical anti-oxidants are organic compounds containing sulfur, phosphorus or nitrogen, such as organic amines, sulfides, hydroxysulfides, methanols, etc., alone or in combination with metals such as zinc, tin or barium. Particularly useful anti-oxidants include phenyl-alpha-naphthylamine, bis(alkylphenyl)amine, N,N'-diphenyl-p-phenylenediamine, 2,2,4-trimethyldihydroquinoline oligomer, bis(4-isopropylaminophenyl)ether, N-acylaminophenol, N-acylphenothiazines, N-hydrocarbylamides of ethylenediamine tetraacetic acid, alkylphenol-formaldehyde-amine polycondensates, etc.

Another additive which may be employed is a rust inhibitor. The rust inhibitor is employed in all types of lubricants to suppress the formation of rust on the surface of metallic parts. Exemplary rust inhibitors include sodium nitrite, alkenylsuccinic acids and derivatives thereof, alkylthioacetic acid and derivatives thereof, substituted imidazoles, amine phosphates, etc. Another additive which may be incorporated into the lubricant composition of this invention is an anti-corrodant. The anti-corrodant is employed to inhibit oxidation so that the formation of acidic bodies is suppressed and to form films over the metal surfaces which decrease the effect of corrosive materials on exposed metallic parts. Typical anti-corrodants are organic compounds containing active sulfur, phosphorus or nitrogen, such as organic sulfides, phosphides, metal salts of thiophosphoric acid, cyclic and acyclic epoxides and sulfurized waxes, barium phenates and sulfonates, etc. A particularly effective corrosion inhibitor is ammonium dinonylnaphthalenesulfonate.

Other types of lubricating oil additives which may be employed in the practice of this invention include anti-foam agents (e.g., silicones, organic copolymers), stabilizers, anti-stain agents, tackiness agents, anti-chatter agents, dropping point improvers, anti-squawk agents, lubricating color correctors, extreme-pressure agents, odor control agents, dispersants, detergents, etc., as well as other anti-wear agents such as tricresyl phosphate and zinc dithiophosphate esters.

In many instances, it may be advantageous to form concentrates of the phosphate salt within a carrier liquid. The employment of concentrates provides a convenient method of handling and transporting the phosphate salts for their subsequent dilution and use. The concentration of the phosphate salt within the concentrates may vary from 10 to 90 weight percent, although it is preferred to maintain the concentration between about 20 and 80 weight percent.

ILLUSTRATIVE EXAMPLE

To a 1-liter flask is added 109 g (⅓ mol) triphenyl phosphate and 215 g (1 mol) cocoamine (96% n-dodecylamine). The reaction mixture is heated with stirring at 150° C. under nitrogen for 4 hours. Analysis by infrared at the end of 4 hours indicates that little to no reaction has taken place.

EXAMPLE 1

To a 3-liter flask was added 575 g cocoamine (96% n-dodecylamine) and 715 g n-dodecylamine (98% pure) (6 mols total), 652.8 g (2 mols) triphenyl phosphate and 38.4 g (2% by weight) boric acid. The reaction mixture was stirred at 200° C. for 8 hours. Analysis by infrared indicated the reaction is complete. The reaction mixture was then stripped at 200° C. and 3 mm Hg to yield 1177 g of overhead distillate. The residue was then filtered hot through a thin pad of diatomaceous earth to yield 734 g of product. The product contained 3.48% nitrogen, 7.55% phosphorus, and had an alkalinity value of 67.2 mg KOH/g.

EXAMPLE 2

To a 500-ml flask was added 163.2 g (0.5 mol) triphenyl phosphate and 107.5 g (0.5 mol) cocoamine (96% n-dodecylamine) and 10.8 g (4 weight percent) boric acid. The reaction mixture was stirred at 130° C. for 10 hours. The reaction mixture was then stripped at 165° C. and 3 mm Hg to yield 197.9 g of product.

EXAMPLE 3

To a 2-liter flask was added 326.3 g (1 mol) triphenyl phosphate, 645 g (3 mols) cocoamine (96% n-dodecylamine) and 39 g (4 weight percent) boric acid. The reaction mixture was stirred at 120° C. for 10 hours under a nitrogen atmosphere. The mixture was then stripped to 165° C. at 4 mm Hg, yielding 571.8 g of product.

EXAMPLE 4

To a 1-liter flask was added 108.8 g (⅓ mol) triphenyl phosphate, 215 g (1 mol) cocoamine (96% n-dodecylamine) and 16 g (5 weight percent) boric acid. The reaction mixture was stirred under nitrogen at 150° C. for 4 hours. Analysis by infrared indicated that the reaction was essentially complete after 30 minutes. The reaction mixture was stripped to 150° C. at 8 mm Hg.

The analysis of the products from Examples 1–4, as done by phosphorus magnetic resonance, is shown in Table I below.

Table I

| Product | Molar percentage distribution in final product prepared by Example: | | | |
|---|---|---|---|---|
| | 1 | 2 | 3 | 4 |
| φO—P(=O)—(NHR)$_2$ | 4 | 0 | 0 | 0 |
| [(φO)$_2$P(=O)]$_2$NR | 5 | 0 | 0 | 0 |
| (φO)$_2$P(=O)—NHR | 5 | 2 | 3 | 15 |
| (φO)$_2$P(=O)—ONH$_3$R (salt) | 38 | 71 | 92 | 74 |
| (φO)$_3$P=O (Starting material) | 1 | 27 | 5 | 0 |
| Other product | 47 | 0 | 0 | 11 |

EXAMPLE 5

The coefficient of friction of a lubricating oil containing the additive prepared by the process of Example 3 is tested in the Kinetic Oiliness Testing Machine (KOTM) manufactured by G. L. Neeley of Berkeley, California. The procedure used in this test is described by G. L. Neeley, Proceedings of Mid-Year Meeting, American Petroleum Institute, 1932, pp. 60–74. Friction was measured in this test under boundary conditions with a load of 100 pounds (12 MPa), speed of 0.1 rpm (0.5 mm/sec). The oil being tested is an SAE 10W40 oil containing 8.4% of a polymethacrylate viscosity index improver and also containing a conventional polybutene succinimide dispersant, zinc dialkyl dithiophosphate and overbased magnesium sulfonate. The results in Table II below show good reduction in the coefficient of friction on both metal combinations tested and at all temperatures tested.

TABLE II
Effect of Product of Example 3 on Coefficient of Friction

| Metal Surfaces | Wt.% Product of Ex.3 | Coefficient of Friction at | | | |
|---|---|---|---|---|---|
| | | 50° C | 100° C | 150° C | 200° C |
| Chromium sliders on Cast Iron Track | 0 | 0.13 | 0.13 | 0.13 | 0.14 |
| | 1 | 0.11 | 0.10 | 0.11 | 0.12 |
| 52100 Steel Sliders on Cast Iron Track | 0 | 0.14 | 0.13 | 0.13 | 0.15 |
| | 1 | 0.10 | 0.080 | 0.082 | 0.099 |

What is claimed is:

1. A process for preparing a phosphate salt which comprises heating a triaryl phosphate and a primary or secondary aliphatic amine in the molar ratio of 1:1–20 respectively at a temperature of 100°–200° C. for 0.5–30 hours in the presence of a catalytic amount of boric acid to yield said phosphate salt.

2. The process of claim 1 wherein the triaryl phosphate has the formula

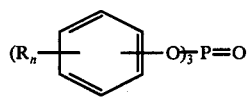

where R is alkyl, halo, alkoxy, nitro, trifluoromethyl, or dihydrocarbyl amino, $n$ is 0, 1 or 2, and the aliphatic amine has the formula

where $R^1$ is an aliphatic radical containing 4–18 carbon atoms and $R^2$ is hydrogen or an aliphatic radical containing 4–18 carbon atoms, and 1–5 weight percent boric acid is employed.

3. The process of claim 2 wherein 3–5% boric acid is employed and the molar ratio of phosphate to amine is about 1:2–3.

4. The process of claim 3 wherein R is alkyl, $R^1$ is alkyl of 12–18 carbon atoms, and $R^2$ is hydrogen.

5. The product prepared by the process of claim 1.

6. The product prepared by the process of claim 4.

7. A lubricating oil composition comprising an oil of lubricating viscosity and from 0.01 to 10% by weight of the product of claim 6.

8. A lubricating oil concentrate comprising from 10–90% by weight of an oil of lubricating viscosity and from 90–10% by weight of the product of claim 6.

9. A method for reducing the friction between relatively moving parts comprising lubricating said parts with the lubricating oil composition of claim 7.

* * * * *